United States Patent [19]

Frenette et al.

[11] Patent Number: 4,918,092
[45] Date of Patent: Apr. 17, 1990

[54] LEUKOTRIENE ANTAGONISTS

[75] Inventors: Richard Frenette, Laval; Robert N. Young, Senneville; Masatoshi Kakushima, Dollard des Ormeaux, all of Canada

[73] Assignee: Merck Frosst Canada, Inc., Kirkland, Canada

[21] Appl. No.: 144,343

[22] Filed: Jan. 15, 1988

Related U.S. Application Data

[63] Continuation of Ser. No. 563,728, Dec. 21, 1983, abandoned.

[51] Int. Cl.$^4$ .............................................. A61K 31/35
[52] U.S. Cl. ...................... 514/382; 514/452; 514/450; 514/456; 514/464; 514/465; 514/466; 514/469; 514/470; 548/253; 549/10; 549/11; 549/350; 549/362; 549/399; 549/355; 549/407; 549/462; 549/445
[58] Field of Search ............... 549/362, 462, 399, 407, 549/355, 350, 445; 514/452, 464, 382, 450, 456, 465, 466, , 469, 470; 548/253

[56] References Cited

U.S. PATENT DOCUMENTS

| | | | |
|---|---|---|---|
| 3,629,290 | 12/1971 | Cairns | 549/402 |
| 4,036,980 | 7/1977 | Schaub et al. | 549/362 |
| 4,193,787 | 3/1980 | Baker | 549/362 |
| 4,423,237 | 12/1983 | Baker | 549/362 |
| 4,659,737 | 4/1987 | Kabbe et al. | 549/362 |

FOREIGN PATENT DOCUMENTS

| | | |
|---|---|---|
| 56172 | 7/1982 | European Pat. Off. |
| 61800 | 10/1982 | European Pat. Off. |
| 2058785 | 4/1981 | United Kingdom |
| 2118184 | 10/1983 | United Kingdom |

OTHER PUBLICATIONS

Samuelsson, B. *Science* vol. 220, pp. 568–575 (1983).
Bailey, D. M. *Annual Reports in Medicinal Chemistry* pp. 203–217 (1982).

*Primary Examiner*—Glennon H. Hollrah
*Assistant Examiner*—Amelia A. Owens
*Attorney, Agent, or Firm*—Gabriel Lopez; Hesna J. Pfeiffer

[57] ABSTRACT

Compounds having the formula I:

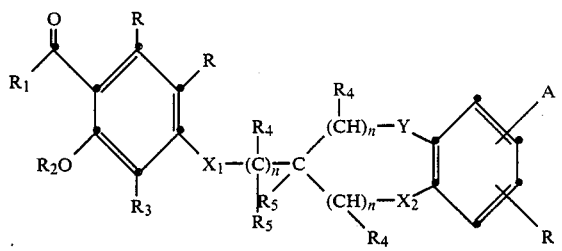

are antagonists of leukotrienes of $C_4$, $D_4$ and $E_4$, the slow reacting substance of anaphylaxis. These compounds are useful as anti-asthmatic, anti-allergic and anti-inflammatory agents.

7 Claims, No Drawings

LEUKOTRIENE ANTAGONISTS

This is a continuation of application Ser. No. 563,728, filed Dec. 21, 1983, now abandoned.

BACKGROUND OF THE INVENTION

This invention is directed to compounds which act as antagonists of the leukotrienes.

The leukotrienes are a novel group of biologically active mediators derived from arachidonic acid through the action of lipoxygenase enzyme systems. There are two groups of leukotrienes derived from the common unstable precursor Leukotriene $A_4$. The first of these are the peptido-lipid leukotrienes, the most important being Leukotrienes $C_4$ and $D_4$. These compounds collectively account for the biologically active material known as the slow reacting substance of anaphylaxis.

The leukotrienes are potent smooth muscle contracting agents, particularly on respiratory smooth muscle but also on other tissues (e.g. gall bladder). In addition, they promote mucous production, modulate vascular permeability changes and are potent inflammatory agents in human skin. The most important compound in the second group of leukotrienes is Leukotriene $B_4$, a dihydroxy fatty acid. This compound is a potent chemotactic agent for neutrophils and eosinophils and in addition, may modulate a number of other functions of these cells. It also effects other cell types such as lymphocytes and for example may modulate the action of T-suppressor cells and natural killer cells. When injected in vivo, in addition to promoting the accumulation of leukocytes, Leukotriene $B_4$ is also a potent hyperalgesic agent and can modulate vascular permeability changes through a neutrophil dependent mechanism. Both groups of leukotrienes are formed following oxygenation of arachidonic acid through the action of a 5-lipoxygenase enzyme. See for example, D. M. Bailey et al., *Ann. Rpts. Med. Chem.* 17 203 (1982).

Respiratory Conditions (a) Asthma. The leukotrienes are potent spasmogens of human trachea, bronchus and lung parenchymal strips, and when administered to normal volunteers as aerosols are 3,800 times more potent that histamine at inducing a 50% decrease in air flow at 30% of vital capacity. They mediate increases in vascular permeability in animals and promote mucous production in human bronchial explants (?). In addition, Leukotriene $B_4$ may also mediate mucous production and could be an important mediator of neutrophil and eosinophil accumulation in asthmatic lungs. 5-lipoxygenase products are also thought to be regulators of mast cell degranulation. In vitro studies have shown that antigen challenge of human lung results in the release of leukotrienes and in addition purified human mast cells can produce substantial amount of leukotrienes. There is therefore good evidence that leukotrienes are important mediators of human asthma. Leukotriene antagonists would therefore be a new class of drugs for the treatment of asthma.

Skin Diseases (a) Psoriasis. Psoriasis is a human skin disease which effects between two and six percent of the population. There is no adequate therapy for psoriasis and related skin conditions. The evidence for leukotriene involvement in these diseases is as follows. One of the earliest events in the development of preparpillary lesions is the recruitment of leukocytes to the skin site. Injection of Leukotriene $B_4$ into human skin results in a pronounced neutrophil accumulation. There are gross abnormalities in arachidonic acid metabolism in human psoriatic skin. In particular, highly elevated levels of free arachidonic acid can be measured as well as large amounts of lipoxygenase products. Leukotriene $B_4$ has been detected in psoriatic lesions, but not in uninvolved skin, in biologically significant amounts.

Allergic Conditions (a) Leukotrienes can be measured in nasal washings from patients with allergic rhinitis and are greatly elevated following antigen challenge. Leukotrienes may mediate this disease through their ability to regulate mast cell degranulation, by modulating mucous production and mucocillary clearance and by mediating the accumulation of inflammatory leukocytes.

Leukotrienes can also mediate other diseases. These include atopic dermatitis, gouty arthritis and gall bladder spasms. In addition, they may have a role in cardiovascular disease because leukotrienes $C_4$ and $D_4$ act as coronary and cerebral arterial vasoconstrictors and these compounds may also have negative ionotropic effects on the myocardium. In addition, the leukotrienes are important mediators of inflammatory diseases through their ability to modulate leukocyte and lymphocyte function. See for example, B. Samuelsson, *Science,* 220 568 (1983).

Several classes of compounds exhibit ability to antagonize the action of leukotrienes in mammals, especially humans. See for example: Great Britain patent specification No. 2,058,785; and European Patent Application Nos. 56,172 and 61,800.

SUMMARY OF THE INVENTION

The present invention provides compounds that act as antagonists to prevent leukotriene action or as inhibitors to prevent synthesis. The present invention also provides compounds which prevent or reverse leukotriene action or prevent leukotriene synthesis when administered orally. The present invention also provides compounds which prevent or reverse leukotriene action or prevent leukotriene synthesis when administered by insufflation, intravenously, rectally, topically, parenterally including subcutaneously and intramuscularly, or nasally. The present invention also provides for the preparation of these compounds. The present invention also provides intermediates useful in the synthesis of these compounds. Finally, the present invention provides pharmaceutical formulations for administering these compounds.

DETAILED DESCRIPTION

The present invention relates to compounds having activity as leukotriene antagonists, to methods for their preparation, to intermediates useful in their preparation and to methods for using these compounds. Because of their activity as leukotriene antagonists, the compounds of the present invention are useful as anti-asthmatic, anti-allergic, and anti-inflammatory agents and are useful in treating allergic rhinitis and chronic bronchitis and for amelioration of skin diseases like psoriasis and atopic eczema. These compounds are also useful to antagonize or inhibit the pathologic acitions of leukotrienes on the cardiovascular and vascular systems.

The compounds of the present invention have the formula I:

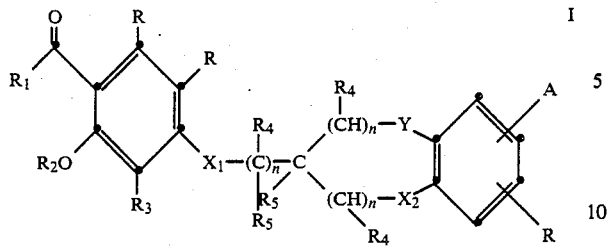

wherein
- each R is independently H, OH, alkyl of 1 to 6 carbon atoms which may be straight chain or branched; alkenyl of 2 to 6 carbon atoms which may be straight chain or branched; trifluoromethyl; alkoxy of 1 to 6 carbon atoms which may be straight chain or branched; SH; thioalkyl of 1 to 6 carbon atoms which may be straight chain or branched; phenyl; phenyl substituted by alkyl of 1 to 3 carbon atoms or by halogen; benzyl; phenethyl; halogen, amino; $N(R_4)_2$ wherein each $R_4$ is independently H or alkyl of 1 to 6 carbon atoms which may be straight chain or branched; phenyl; $COOR_4$; $CH_2OR_4$; formyl; CN; trifluoromethylthio; or nitro;
- $R_1$ is H, alkyl of 1 to 6 carbon atoms which may be straight chain or branched; or alkoxy of 1 to 6 carbon atoms which may be straight chain or branched;
- $R_2$ is H, alkyl of 1 to 6 carbon atoms which may be straight chain or branched; $R_4CO$; or $R_4OCH_2$;
- $R_3$ is alkyl of 1 to 6 carbon atoms which may be straight chain or branched; or alkenyl of 3 to 6 carbon atoms which may be straight chain or branched;
- $X_1$ to $X_2$ are independently oxygen, sulfur, sulfoxide, sulfone;

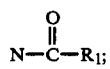

$NR_4$;

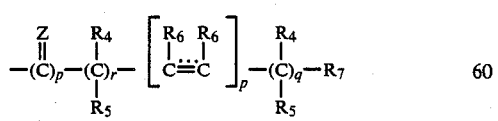

N—CN; or $NCONHR_4$;
Y is $X_1$, $X_2$ or $CHR_4$;
A is

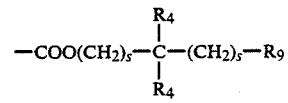

wherein
Z is O; S; H/OH; $CH_2$; alkenyl of 1–4 carbons; or $N-R_8$ wherein $R_8$ is OH, $N(R_4)_2$, alkyl or alkoxy of 1 to 6 carbon atoms, phenyl or phenyl substituted by alkyl or alkoxy groups of 1 to 3 carbon atoms, halogen, hydroxy, haloalkyl, COOH, CN, formyl or acyl of 1 to 6 carbon atoms;
- each $R_5$ is independently H, OH, or alkyl of 1–4 carbons;
- each $R_6$ is independently H, or alkyl of 1–4 carbons, and is absent when a triple bond is present;
- $R_7$ is $COOR_4$; $CH_2OH$; CHO; tetrazole; $CONHSO_2R_8$; $NHSO_2R_8$; hydroxymethylketone; CN; $CON(R_4)_2$; a monocyclic or bicyclic heterocyclic ring containing an acidic hydroxyl group; or $$-COO(CH_2)_s-\underset{\underset{R_4}{|}}{\overset{\overset{R_4}{|}}{C}}-(CH_2)_s-R_9$$

wherein each s is independently 0–3; $R_9$ is
(A) a monocyclic or bicyclic heterocyclic radical containing from 3 to 12 nuclear carbon atoms and 1 or 2 nuclear heteroatoms selected from N and S with at least one being N, and with each ring in the heterocyclic radical being formed of 5 or 6 atoms, or
(B) the radical $W-R_{10}$ wherein W is O, S or NH and $R_{10}$ contains up to 21 carbon atoms and is (1) a hydrocarbon radical or (2) an acyl radical of an organic acyclic or monocyclic carboxylic acid containing not more than 1 heteroatom in the ring;

r and q are each independently 0–20 provided that the total of r and q does not exceed 20; and
each n is independently 0, 1, 2 or 3;
p is 0 or 1;
and a pharmaceutically acceptable salt or acid addition salt thereof.

A preferred embodiment of the present invention are compounds having the formula Ia:

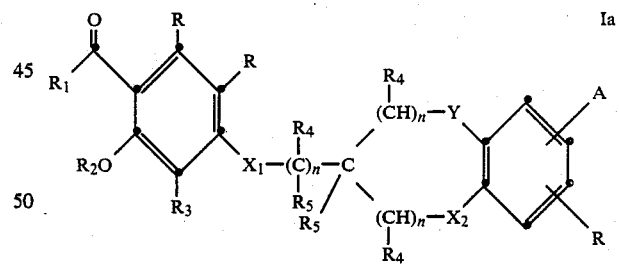

wherein:
$X_1$ and $X_2$ are independently oxygen, sulfur, sulfoxide or sulfone;
A is

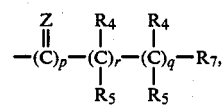

wherein
Z is O; S; H and OH; or $N-R_8$;
r and q are each independently 0–5;
and all other definitions are as for formula I.

SCHEME I

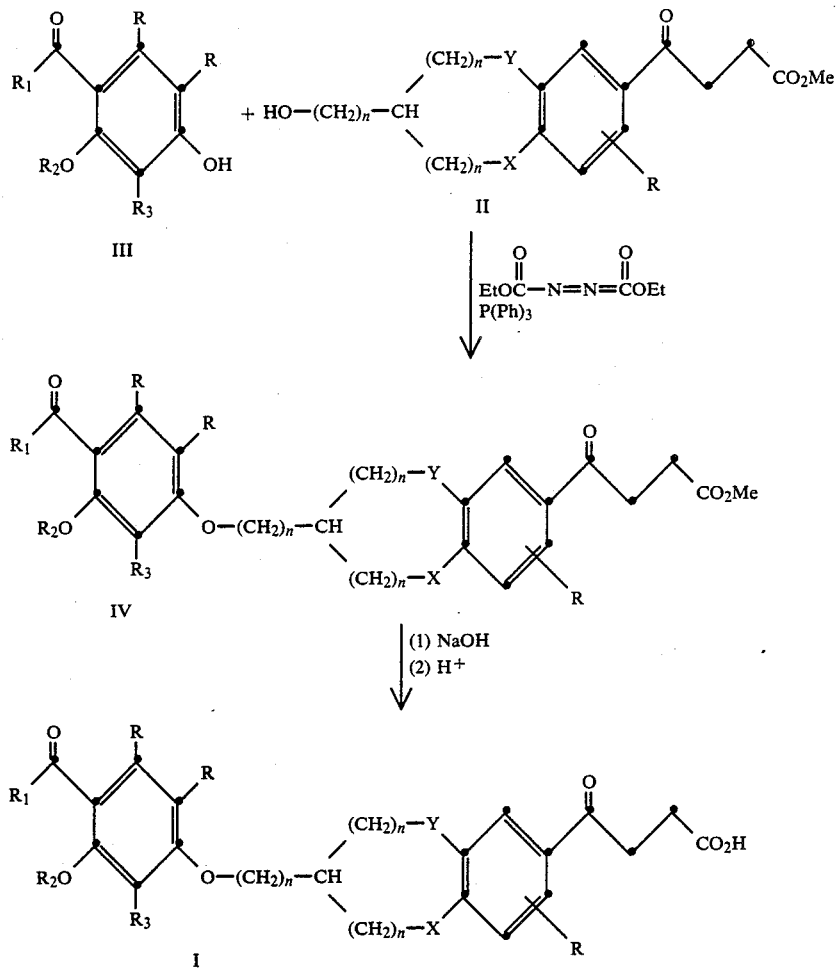

The compounds of the present invention may be prepared by several different routes. According to one method, illustrated in Scheme I, a compound of formula II is reacted with a suitable compound III using diethyl diazodicarboxylate and triphenylphospine, according to O. Mitsumobo, *Syntheis* 1 (1981), to yield the novel intermediate IV. An alternate procedure to IV involves the displacment of the mesylate or arylsulfonate of II, or its corresponding chloride, bromide, iodide by III in the presence of a base, such as potassium carbonate in a solvent such as methyl ethyl ketone. Other suitable bases could be an alkali metal carbonate such as $Li_2CO_3$, or $Na_2CO_3$. The reaction could also be carried out in other solvents such as THF, glyme, diglyme on DMF. The temperature range to carry out this transformation is 25°-160° C., the optimum being 60°-70° C.

Compound IV is then hydrolyzed with a suitable base such as aqueous sodium hydroxide and the free acid of formula I is recovered by acidification.

SCHEME II

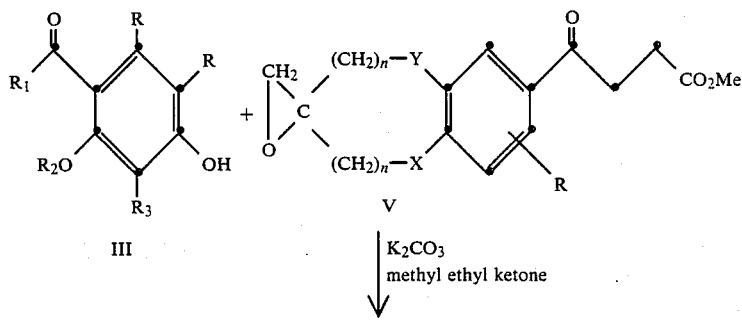

SCHEME II

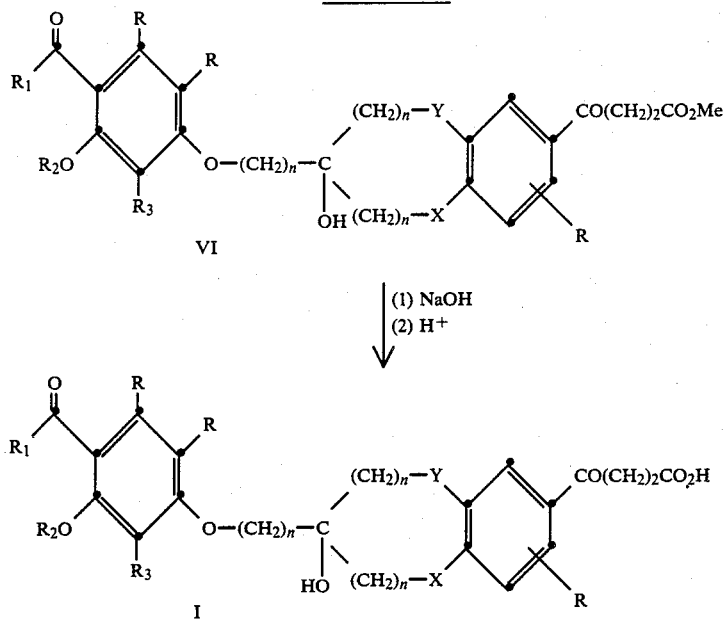

An alternate preparation of I as illustrated in Scheme II involves the reaction of III with V in the presence of an anhydrous base such as K$_2$CO$_3$, Na$_2$CO$_3$ and the like, in a suitable solvent such as methylethyl ketone, dimethylformamide, tetrahydrofuran and the like, to provide the intermediate of formula VI. Compound VI is the hydrolyzed with an aqueous base such as sodium or potassium hydroxide, and, following acidification, the compound of formula I is obtained.

Certain of the compounds described herein possess one or more asymetric centers, and thus may exist as diastereoisomers and optical isomers. The present invention includes all individual diastereoisomers as well as the racemic and optically resolved isomers of a given compound.

In those instances when asymmetric carbon atoms are present, more than one stereoisomer is possible, and all possible isomeric forms are deemed to be included within the planar structural representations shown. Optically active (R) and (S) isomers may be resolved using conventional techniques known to the skilled artisan.

The magnitude of a prophylactic or therapeutic dose of a compound of formula I will, of course, vary with the nature of the severity of the condition to be treated and with the particular compound of formula I and its route of administration. In general, the daily dose range lies within the range of from about 0.2 mg to about 100 mg per kg body weight of a mammal.

The pharmaceutical compositions of the present invention comprise a compound of formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. The compositions include compositions suitable for oral, rectal, ophthalmic, pulmonary, nasal, dermal, topical or parenteral (including subcutaneous, intramuscular and intravenous) administration, although the most suitable route in any given case will depend on the nature and severity of the conditions being treated and on the nature of the active ingredient. They may be conveniently presented in unit dosage form and prepared by any of the methods well-known in the art of pharmacy.

For use where a composition for intravenous administration is employed, a suitable dosage range is from about 0.01 to about 20 mg (preferably from about 0.1 to about 10 mg) of a compound of formula I per kg of body weight per day and in the case where an oral composition is employed a suitable dosage range is, e.g. from about 1 to about 100 mg of a compound of formula I per kg of body weight per day, preferably from about 5 to about 40 mg per kg.

For administration by inhalation, the compounds of the present invention are conveniently delivered in the form of an aerosol spray presentation from pressurized packs or a nebuliser. The preferred composition for inhalation is a powder which may be formulated as a cartridge from which the powder composition may be inhaled with the aid of a suitable device. In the case of a pressurized aerosol, the dosage unit may be determined by providing a valve to deliver a metered amount.

Pharmaceutical compositions of the present invention suitable for oral administration and by inhalation in the case of asthma therapy may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Molded tablets may be made by molding in a suitable machine, a mixture of the powdered compound moistened with an inert liquid diluent. Desirably, each tablet contains from about 25 mg to about 500 mg of the active ingredient and each cachet or capsule contains from about 25 to about 500 mg of the active ingredient.

The following examples illustrate the present invention without, however, limiting the same thereto. All temperatures are expressed in degrees Celsius.

EXAMPLE 1

Methyl 4-(4-hydroxy-3-formylmelthylphenyl)-4-oxo-butyrate

Ozone was bubbled through a solution of methyl 4-(4-hydroxy-3-(2-propenyl)phenyl)-4-oxo-butyrate (10 g, 0.0402 moles) in 200 ml $CH_2Cl_2$ at $-78°$ C. for 80 minutes. The reaction mixture was flushed at $-78°$ with $N_2$ for 20 minutes then 10 ml $(CH_3)_2S$ was added and the mixture was warmed to room temperature with $N_2$ flow overnight. The reaction mixture was concentrated to afford the title compound which was used without further purification.

EXAMPLE 2

Methyl 4-(2-formylmethyl-2,3-dihydrobenzo[b]furan-5-yl)-4-oxobutyrate

The compound of Example 1, (14 g crude-about 10 g pure) was taken up in about 100 ml $CHCl_3$ to which was added formylmethylenetriphenylphosphorane (12.20 g) and the reaction mixture was stirred at room temperature under $N_2$ for 2 hours. The reaction mixture was then heated at 50° for 1 hour. Additional formylmethylenetriphenylphosphorane (3 g) was added and the reaction mixture was stirred at room temperature for one hour. The reaction mixture was concentrated and the crude title compound was passed over silica gel using 8/2 $CHCl_3$/EtOAc. The residue was taken up in ether, from which triphenylphosphine oxide crystallized and was filtered off. The crude title compound was obtained by evaporation of the ether.

EXAMPLE 3

Methyl 4-(2-(2-hydroxyethyl)-2,3k-dihydrobenzo[b]furan-5-yl)-4-oxobutyrate

The crude compound from Example 2 (4.2 g, contains about 50% triphenylphosphine oxide was taken up in about 40 ml absolute ethanol and cooled to 0° under $N_2$. $NaBH_4$ (80 mg) was added and the reaction mixture was stirred 1 hour at 0°. $H_2O$ (40 ml) containing several drops of concentrated HCl was added to the reaction mixture which was extracted into $CHCl_3$. The $CHCl_3$ extract was dried and concentrated. The crude residue was purified on HPLC using 8/2 $CHCl_3$/ethyl acetate, to afford the title compound as a solid, m.p. 64°–66°.

EXAMPLE 4

Methyl 4-[2-(2-(4-acetyl-3-hydroxy-2-propylphenoxy)ethyl)-2,3-dihydrobenzo[b]furan-5-yl]-4-oxobutyrate The compound of Example 3, (700 mg, 2.52 mmoles) was combined with 2,4-dihydroxy-3-propylacetophenone (490 mg) in 30 ml dry THF at room temperature under $N_2$. Diethyl azodicarboxylate (DEAD) (475 μl) was added and the reaction mixture was stirred for 15 minutes. Triphenylphosphine (791 mg) was added and the reaction mixture was stirred overnight at room temperature. The reaction was concentrated and purified on HPLC. The title compound was recrystallized from $CHCl_3$/ether. NMR (90 MHz) ($CDCl_3$) (ppm): 0.9 ppm (3H, t), 1.6 ppm (2H, m), 2.3 ppm (2H, m), 2.6 ppm (3H, s), 2.7 ppm (4H, 2t), 3.3 ppm (4H, m), 3.7 ppm (3H, s), 4.3 ppm (2H, m), 3.7 ppm (3H, s), 4.3 ppm (2H, m), 5.2 ppm (1H, m), 6.4 ppm (1H, d), 6.8 ppm (1H, d), 7.7 ppm (1H, d), 7.9 ppm (2H, m), 12.7 ppm (1H, s) (exchangeable with $D_2O$).

EXAMPLE 5

4-[2-(2-(4-acetyl-3-hydroxy-2-propylphenoxy)ethyl)-2,3-dihydrobenzo[b]furan-5-yl]-4-oxobutyric acid The compound of Example 4 (275 mg, 0.61 mmoles) was taken up in approximately 5 ml THF to which was added in NaOH (1.3 ml). After 2 hours, the THF was removed in vacuo and the aqueous phase was diluted with two volumes of distilled $H_2O$ acidified with concentrated HCl. The title compound was extracted into $CHCl_3$, dried and concentrated to a beige solid, m.p. 156°–158°

Analysis, calculated for $C_{25}H_{28}O_7$: C, 68.17; H, 6.41. Found: C, 68.20; H, 6.23.

EXAMPLE 6

Methyl (4-hydroxy-3-(4-hydroxy-2-butenyl)phenyl)acetate

The compound of Example 17 (2.7 g, 0.013 moles) was taken up in about 50 ml dry $CH_2Cl_2$ to which was added formylmethylenetriphenylphosphorane (8.0 g). The reaction mixture was stirred at room temperature under $N_2$ for 2 hours. The reaction mixture was concentrated, taken up in a mixture of isopropanol (60 ml) and $H_2O$ (15 ml). $CeCl_3$ (9 mg) was added and the reaction mixture, after stirring 5 minutes at room temperature, was cooled to 0°. $NaBH_4$ (2.2 g) was added in about 50 mg portions via a solid addition apparatus, over a period of 2 hours. The reaction mixture was poured into one liter of ether then filtered and concentrated. The residue was taken up in CH₂Cl₂ and washed with 1N HCl, dried and concentrated. The title compound was purified on a silica gel column using ethyl acetate and repurified using HPLC eluting with 1/1 ethyl acetate/hexane. NMR (90 MHz) (CDCl₃) (ppm): 2.4 (1H, br), 3.30 (2H, d), 3.50 (2H, s), 3.65 (3H, s), 4.00 (2H, d), 5.70 (2H, m), 6.5 (1H, br), 6.6–7.0 (3H, m).

EXAMPLE 7

Methyl (2-(1,2-dihydroxyethyl)-2,3-dihydrobenzo[b]furan-5-yl)acetate

The compound of Example 6, (700 mg, 3.0 mmoles) was taken up in about 15 ml CH₂Cl₂ and cooled to 0° under N₂. m-Chloroperbenzoic acid (m-CPBA) was added (660 mg) to the solution and the reaction mixture was stirred 1 hour at 0°. Additional m-CPBA (70 mg) was added and the reaction mixture was stirred for 21 hours at room temperature. Ca(OH)₂ (650 mg) was added and the reaction mixture was stirred for 10 minutes then filtered through Celite and concentrated. The residue was taken up in ethyl acetate (10 ml) with Et₃N (2 ml) and stirred at room temperature overnight. The concentrate was then concentrated to dryness. Chromatography of the residue on silica gel using ethyl acetate gave the title compound. NMR (90 MHz) (CDCl₃) (ppm): 2.5–3.1 (2H, br), 3.20 (2H, d), 3.50 (2H, s), 3.65 (3H, s), 3.6–4.0 (3H, m), 4.70 (1H, m), 6.67 (1H, d), 6.8–7.1 (2H, m).

EXAMPLE 8

Methyl [2-(1-hydroxy-2-(2,4,6-trimethylphenylsulfonyloxy)ethyl)-2,3-dihydrobenzo[b]furan-5-yl]acetate The compound of Example 7, (430 mg, 1.7 mmoles) was taken up in dry pyridine (20 ml) and cooled to 0° under N₂. 2,4,6-Trimethylphenylsulfonyl chloride (400 mg) was added at 0° and stirring was continued overnight at 0°. Additional 2,4,6-trimethylphenylsulfonyl chloride (75 mg) was added, and stirring was continued at 5° for 24 hours. The pyridine was removed under high vacuum and the residue was taken up in CHCl₃, washed with dilute HCl, brine, dried and concentrated. Chromatography of the residue on silica gel using ethyl acetate gave the title compound as a mixture of the two diastereoisomers. NMR (90 MHz) (CDCl₃) (ppm) 2.37 (3H, s), 2.67 (6H, s), 2.5–2.8 (1H, br), 3.27 (2H, d), 3.57 (2H, s), 3.70 (3H, s), 3.9–4.3 (3H, m), 4.75 (1H, m), 6.73 (1H, d), 6.97–7.25 (4H, m).

EXAMPLE 9

Methyl (2-(1,2-oxidoethyl)-2,3-dihydroxybenzo[b]furan-5-yl)acetate

The compound of Example 8, (700 mg, 1.611 mmoles) was taken up in dry CH₃OH (20 ml) under N₂. CH₃ONa (1.1 equiv.) was added. After 1 ice was added, then brine and the reaction mixture was extracted into CHCl₃ (10×20 ml) then dried and concentrated to yield the title compound as a mixture of the two diastereoisomers which could be seen in its ¹H NMR spectrum. NMR (90 MHz) (CDCl₃) (ppm): 2.5–2.9 (3H, m), 3.10–3.35 (2H, two sets of doublets), 3.50 (2H, s), 3.70 (3H, s), 4.75 (1H, m), 6.80 (1H, d), 7.0–7.2 (2H, m).

EXAMPLE 10

Methyl [2-(1-hydroxy-2-(4-acetyl-3-hydroxy-2-propylphenoxy))ethyl-2,3-dihydrobenzo[b]furan-5-yl]acetate The compound of Example 9, (about 470 mg, 1.7 mmole) was combined with 2,4-dihydroxy-3-propylacetophenone (360 mg) and K₂CO₃ (250 mg) in melthylethyl ketone (MEK) (50 ml). The reaction mixture was refluxed under N₂ overnight. The reaction mixture was filtered and purified on a silica gel column using 1/1 ethyl acetate hexane to give the title compound as a mixture of the two diastereoisomers.

NMR (90 MHz) (CDCl₃) (ppm): 0.9 (3H, t), 1.6 (2H, s), 2.6 (3H, d), 2.7 (2H, s), 2.8 (3H, m), 3.6 (2H, d), 3.8 (3H, s), 4.0 (2H, s), 4.6 (1H, broad s), 5.4 (1H, m), 7.1 (1H, d), 7.4 (1H, d), 7.8 (2H, m), 8.4 (1H, d), 13.2 (1H, s).

EXAMPLE 11

[2-(1-Hydroxy-2-(4-acetyl-3-hydroxy-2-propylphenoxy))ethyl-2,3-dihydrobenzo[b]furan-5-yl]acetic acid The compound of Example 10, (350 mg, 0.818 mmoles) was taken up in THF (5 ml) to which was added 1N NaOH (2 ml) and H₂O (3 ml). The reaction mixture was stirred at room temperature under N₂ for 2 hours. The THF was removed in vacuo. The residue was diluted with H₂O (20 ml), then extracted with CHCl₃ (2×10 ml). The aqueous phase was acidified with concentrated HCl then extracted into CHCl₃. The organic extracts were dried and concentrated. The residue was crystallized from ether to afford the title compound as a mixture of the two diastereoisomers, m.p. 112°–114°.

Analysis, calculated for C₂₃H₂₆O₇: C, 66.65; H, 6.32. Found: C, 66.53; H, 6.41.

EXAMPLE 12

Methyl 4-(4-(2-propenyl)oxyphenyl)-4-oxobutyrate

To a cooled solution of methyl 4-(4-hydroxy)phenyl-4-oxobutyrate (15 g) in anhydrous DMF (200 ml) was added in 2 portions 99% NaH (2.08 g). The reaction mixture was stirred at OC under N₂ for 1 hour. To this cooled solution was added allyl bromide (8.7 ml) and the mixture was stirred at room temperature for 1 hour. The reaction mixture was poured in H₂O (800 ml) and extracted with Et₂O three times. The combined organic layers were washed with H₂O, brine, dried and evaporated to give an oil which was purified on a preparative HPLC (Waters 500) using 10:3 hexane/ethyl acetate as eluant to give the title compound. NMR (90 MHz) (CDCl₃) (ppm): 2.7.0 (2H, t), 3.23 (2H, t), 3.67 (3H, s), 4.57 (2H, d), 5.2–5.5 (2H, m), 5.8–6.2 (1H, m), 6.90 (2H, d), 7.95 (2H, d).

EXAMPLE 13

Methyl 4-(4-(4-hydroxy-3-allyl-(2-propenyl)oxyphenyl)-4-oxobutyrate

The compound of Example 12, (16.5 g) was heated at 200° in dichlorobenzene (11 ml) under N₂ for 15 hours. The reaction mixture was cooled to room temperature and diluted with CH₂Cl₂ (10 ml) and purified on a preparative HPLC (Waters 500) using hexane/ethyl acetate (10:3.5) as eluant, to afford the title compound as a solid, m.p. b 73°–74°.

EXAMPLE 14

Methyl 4-(2-hydroxymethyl-2,3-dihydrobenzo[b]furan-5-yl)-4-oxobutyrate

To a solution of the compound of Example 13 (3 g, 12.1 mmoles), in $CH_2Cl_2$ (30 ml) was added a solution of m-CPBA (3.2 g) in $CH_2Cl_2$ (20 ml). The mixture was stirred at 25° C. for 17 hours. $Ca(OH)_2$ (1.2 g) was added and the mixture was stirred for 15 minutes. The solid was removed by filtration and the filtrate was washed first with brine containing $Na_2SO_3$ (10% solution), then with brine. The organic layer was dried ($Na_2SO_4$) and concentrated to give an oil. Chromatography on a preparative HPLC (Waters 500) using hexane/ethyl acetate (1:2) gave the title compound as an oil which crystallized, m.p. 70°–72°.

EXAMPLE 15

Methyl 4-(2-(4-acetyl-3-hydroxy-2-propylphenoxymlethyl)-2,3-dihydrobenzo[b]furan-5-yl)-4-oxobutyrate To a solution of the compound of Example 14 (1.5 g) and 2,4-dihydroxy-3-propylacetophenone (1.1 g) in dry THF (30 ml) in an atmosphere of $N_2$ at 0° was added DEAD (1.34 ml). To this solution was added $Ph_3P$ (2.28 g). The reaction mixture was stirred at 25° C. for 49 hours, then concentrated in vacuo and chromatographed in a column of silica gel (70–230 mesh) eluting with EtOAc-toluene (1:10, with the amount of EtOAc increased gradually to a final ratio of 2:10). The fractions containing the title compound were combined and concentrated. Preparative HPLC (Waters 500), eluting with hexane-ethyl acetate (2:1) gave the title compound as an oil.

Analysis, calculated for $C_{25}H_{28}O_7$: C, 68.17; H, 6.41. Found: C, 68.22; H, 6.41.

EXAMPLE 16

4-(2-(4-Acetyl-3-hydroxy-2-propylphenoxymethyl)-2,3-dihydrobenzo[b]furan-5-yl)-4-oxobutyric acid A solution of the methyl ester from Example 15 (800 mg) in a mixture of THF (10 ml), MeOH (4 ml) and 1N NaOH (4 ml) was stirred at room temperature for 4 hours and then diluted with $H_2O$ (30 ml). 1N HCl was added to bring the pH to about 7. The mixture was extracted with $MeOH-CHCl_3$ (1:9) (50 ml ×2) and the extracts were washed with brine, dried over $Na_2SO_4$ and filtered. The filtrate was concentrated to dryness and crystallized from $CH_2Cl_2$. The crystals were collected, washed with $CH_2Cl_2$ and dried at 25° (0.8 mmHg) for 12 hours, to afford the title compound, m.p. 80°.

Analysis calculated for $C_{24}H_{26}O_7 \cdot (H_2O)_3$: C, 59.99; H, 6.71. Found: C, 60.04; H, 6.57.

EXAMPLE 17

Methyl (4-hydroxy-3-formylmelthylphenyl)acetate

A solution of methyl 4-hydroxy-3-allylphenylacetate (10.0 g) in $CH_2Cl_2$ (200 ml) was cooled in a dry-ice bath under an atmosphere of $N_2$. A stream of $O_3$ in oxygen was bubbled into the colorless solution while stirring for 1 hour, which resulted in a clear yellow solution. The reaction mixture was flushed with nitrogen for 20 minutes and dimethylsulfide (10 ml) was added. The dry-ice bath was removed and the reaction mixture was gradually allowed to warm to room temperature. Removal of the solvent gave the title compound as an oil. NMR ($CDCl_3$) (ppm): 3.53 (2H, s), 3.67 (3H, s), 6.00 (0.85 H, dd, J=7 and 3 Hz), 9.70 (0.15 H, m).

EXAMPLE 18

Methyl (2-(2-hydroxymethyl)-2,3-dihydrobenzo[b]furan-5-yl)acetate

Formylmelthylenetriphenylphosphorane (1.8 g) was added to a solution of the compound of Example 17 (1.25 g) in $CDCl_3$ (10 ml). NMR analysis of the reaction mixture showed that the reaction was completed. This mixture was directly subjected to silica gel column chromatography. The fractions containing the aldehyde were combined and concentrated in vacuo. the recovered aldehyde (0.61 g) was treated with $NaBH_4$ (50 mg) in cold (0°) methanol (3 ml) for 5 minutes. The mixture was diluted with $H_2O$, acidified with 1N HCl, and extracted with $CH_2Cl_2$ (20 ml×3) to give the title compound as an oil.

NMR ($CDCl_3$) (ppm): 2.00 (2H, m), 2.60 (1H, exchangeable in $D_2O$), 3.10 (2H, m), 3.53; (2H, s) 3.70 (3H, s), 3.85 (2H, t, J=7 Hz), 4.97 (1H, m), 6.70 (1H, d, J=9 Hz), 6.83–7.17 (2H, m). cl EXAMPLE 19

Methyl [2-(2-(4-acetyl-3-hydroxy-2-propylphenoxy)ethyl)-2,3-dihydrobenzo[b]furan-5-yl]acetate To a solution of the compound of Example 18 (1.05 g) and 2,4-dihydroxy-3-propylacetophenone (0.65 g) in THF (10 ml) was added DEAD (0.85 ml) at room temperature. The solution was cooled to about −5° and triphenylphosphine (1.42 g) was added in one portion. The ice bath was removed and the reaction mixture was stirred at room temperature for 2 hours. The solvent was removed in vacuo and the residue chromatographed on a column of silica gel (20–230 mesh) eluting with toluene-ethyl acetate (10:1) to give the title compound, m.p. 59°–60°.

Analysis, calculated for $C_{24}H_{28}O_6$: C, 69.88; H, 6.84. Found: C, 69.92; H, 6.96.

EXAMPLE 20

[2-(2-(4-acetyl-3-hydroxy-2-propylphenoxy)ethyl)-2,3-dihydrobenzo[b]furan-5-yl]acetic acid To a solution of the compound of Example 19 (429 ml) in THF (10 ml) at room temperature was added 1N NaOH (5.2 ml). MeOH (about 4 ml) was added until the mixture became homogeneous. The resulting solution was stirred at room temperature for one half hour, diluted with $H_2O$ (50 ml) and washed once with ether (50 ml). The aqueous layer was acidified with 6N HCl (1 ml) and the product was extracted into $CH_2Cl_2$. The $CH_2Cl_2$ extracts were washed with brine, dried over $Na_2SO_4$ and concentrated to give the title compound, m.p. 118°–126°.

Analysis, calculated for $C_{23}H_{26}O_6$: C, 69.33; H, 6.58. Found: C, 69.39; H, 6.78.

EXAMPLE 21

Methyl 4-(allyloxyphenyl)acetate

To a cooled (0°) solution of methyl 4-hydroxyphenylacetate (55 g) in dry DMF (400 ml) was added in portions 99% NaH (8.75 g). After the addition the mixture was stirred at room temperature for 45 minutes, (still some NaH in suspension). This mixture was cooled to 0° and allyl bromide (37 ml) was added slowly (Note: exothermic). The reaction mixture was stirred for 10 minutes at 0°, 10 minutes at room temperature and then was stirred for 10 minutes at 60°. The reaction mixture was poured into H$_2$O (1200 ml) and extracted with Et$_2$O (3×400 ml). The combined organic layers are washed with H$_2$O (2×400 ml), dried and evaporated to give an oil. The crude oil was purified by HPLC to afford the title compound as a colorless oil.

NMR (CDCl$_3$) (ppm): 3.5 (s, 2H) 3.7 (s, 3H), 4.5 (d, 2H), 5.15-5.50 (m, 2H), 5.8-6.3 (m, 1H), 6.85 (d, 2H), 7.2 (d, 2H).

EXAMPLE 22

Methyl (4-hydroxy-3-allylphenyl)acetate

A solution of the compound of Example 21 (20 g) in o-dichlorobenzene (23 ml) was heated at 200° under N$_2$ for 20 hours. The reaction mixture was cooled to room temperature, diluted with toluene (30 ml) and purified on a column of silica gel (70-230 mesh, 600 g) using toluene (500 ml) to remove the o-dichlorobenzene and toluene/ethyl acetate (10:1) to elute the title compound as a colorless oil.

NMR (CDCl$_3$) (ppm): 3.35 (d, 2H), 3.55 (s, 2H), 3.7 (s, 3H), 5.15 (d, 2H) 5.55 (s, 1H), 5.8-6.3 (m, 1H), 6.7 (d, 1H), 6.95-7.15 (m, 2H).

EXAMPLE 23

Methyl (4-hydroxy-3-(2,3-oxidopropyl)phenyl)acetate

To a solution of the compound of Example 22 (10 g) in CH$_2$Cl$_2$ (50 ml) was added slowly a solution of 85% m-CPBA (12.8 g) in CH$_2$Cl$_2$ (200 ml). The reaction mixture was stirred at room temperature overnight and a white solid formed. Residual m-CPBA was removed by adding solid Ca(OH)$_2$ (5.4 g) and stirring the mixture at room temperature for 15 minutes. The pink solid was removed by filtration, washed and the filtrate was evaporated to give the title compound as a yellow oil. NMR (CDCl$_3$) (ppm): 2.6-3.0 (m, 4H), 3.05-3.4 (m, 1H), 3.5 (s, 2H), 3.75 (s, 3H), 6.8 (d, 1H), 7.0-7.3 (m,3H).

EXAMPLE 24

Methyl (2-hydroxymethyl-2,3-dihydrobenzo[b]furan-5-yl)acetate

To a solution of the compound of Example 23 (8 g) in THF (80 ml) was added NEt$_3$ (10 ml). The reaction mixture was stirred at room temperature overnight to afford a dark solution. The reaction mixture was evaporated, then coevaporated, with CH$_2$Cl$_2$ and purified by preparative HPLC (Waters 500) using hexane/ethyl acetate (5:4) to afford the title compound as a colorless oil.

Analysis, calculated for C$_{24}$H$_{14}$O$_4$: C, 64.98; H, 6.35. Found: C, 64.85; H, 6.51.

EXAMPLE 25

Methyl (2-(4-acetyl-3-hydroxy-2-propylphenoxy)methyl-2,3-dihydrobenzo[b]furan-5-yl)acetate To a solution of the compound of Example 24 (1.52 g) and 2,4-dihydroxy-3-propylacetophenone (1.33 g) was added, under N$_2$, in dry THF (20 ml), DEAD (1.6 ml), to give an orange solution. The mixture was stirred at room temperature for 15 minutes. To this mixture was added solid triphenylphosphine (2.69 g). The orange solution became a dark red solution in a few seconds and the reaction was exothermic. The reaction mixture was cooled to 0° C. for 5 minutes and then stirred at room temperature for 1 hour. The reaction mixture was evaporated under vacuum and purified by preparative HPLC (Waters 500) using hexane/ethyl acetate (10:4) as eluant. The title compound was obtained as a beige solid by trituration in hexane at 0°, m.p. 77°-78°.

Analysis, calculated for C$_{23}$H$_{26}$O$_6$: C, 69.33; H, 6.58. Found: C, 69.33; H, 6.77.

EXAMPLE 26

(2-(4-acetyl-3-hydroxy-2-propylphenoxy)methyl-2,3-dihydrobenzo[b]furan-5yl)acetate acid To a solution of the compound of Example 25 (760 mg) in THF (10 ml) was added 1N NaOH (4.8 ml). MeOH (1 ml) was added to afford a homogeneous orange solution. The mixture was stirred at room temperature for 1.5 hours. The reaction mixture was diluted with H$_2$O (40 ml), acidified with concentrated HCl (to pH 5) and extracted with CH$_2$Cl$_2$ (twice). The combined organic layers were washed with brine, dried and evaporated to afford the title compound. Chromatography on silica gel (50 g) with CHCl$_3$:CH$_3$OH (100:5) afforded the title compound as a white solid, m.p. 139°-140°.

Analysis, calculated for C$_{22}$H$_{24}$O$_6$: C, 68.73; H, 6.29. Found: C, 68.85; H, 6.16.

Similarly, there were prepared the following compounds, using the general procedures of Examples 21-26, but substituting the appropriate starting materials for methyl 4-hydroxybenzeneacetate.

EXAMPLE 27

Methyl (3-fluoro-4-allyloxyphenyl)acetate

Following the procedure of Example 21, but starting with methyl 3-fluoro-4-hydryoxyphenylacetate there was prepared the title compound. NMR (CDCl$_3$ (ppm): 3.5 (s, 2H), 3.7 (s, 3H), 4.5 (d, 2H), 5.15-5.5 (m, 2H), 5.8-6.3 (m, 1H), 6.8-7.15 (m, 3H).

EXAMPLE 28

Methyl (3-fluoro-4-hydroxy-5-allylphenyl)acetate

Following the procedure of Example 22, but starting with the compound of Example 27, there was obtained the title compound.

NMR (CDCl$_3$) (ppm): 3.35 (d, 2H), 3.55 (s, 2H), 3.7 (s, 3H), 5.15 (d, 2H), 5.8-6.3 (m, 1H), 6.8-7.15 (m, 3H).

EXAMPLE 29

Methyl (3-fluoro-4-hydroxy-5-(2,3-oxidopropyl)phenyl) acetate

Following the procedure of Example 23, but starting with the compound of Example 28, there was obtained the title compound as an oil.

NMR (CDCl$_3$) (ppm): 2.6-3.0 (m, 4H), 3.05-3.4 (m, 1H), 3.5 (s, 2H), 3.7 (s, 3H), 6.7-7.05 (m, 3H) 0.8-7.15 (m, 3H).

EXAMPLE 30

Methyl (2-hydroxymethyl-2,3-dihydro-7-fluorobenzo[b]furan-5yl)acetate

Following the procedure of Example 24, but starting with the compound of Example 29, there was obtained the title compound as a colorless oil.

Analysis calculated for $C_{12}H_{13}O_4F$: C, 60.00; H, 5.45. Found: C. 60.05; H, 5.70.

EXAMPLE 31

Methyl (2-(4-acetyl-3-hydroxy-2-propylphenoxy)methyl-7-fluoro-2,3-dihydrobenzo[b]furan-5-yl)acetate Following the procedure of Example 25, but starting with the compound of Example 30, there was obtained the title compound as a beige solid, m.p. 80°–82°.

Analysis, calculated for $C_{23}H_{25}O_6F$: C, 66.33; H, 6.05. Found: C, 66.38; H, 6.00.

EXAMPLE 32

(3-(4-acetyl-3-hydroxy-2-propylphenoxy)methyl-7-fluoro-2,3-dihydrobenzo[b]furan-5-yl)acetic acid Following the procedure of Example 26, but starting with the compound of Example 31, there was obtained the title compound as a beige solid, m.p. 133°–135°.

Analysis, calculated for $C_{22}H_{23}O_6F$: C, 65.66; H, 5.76. Found: C, 652.82; H, 5.76.

EXAMPLE 33

2- and 3-Hydroxymethyl-2,3-dihydro-1,4-benzodioxin-6-ylacetic acid methyl esters To a solution of methyl 3,4-dihydroxyphenylacetate (3.0 g) in methyl ethyl ketone (70 ml) were added sequentially $K_2CO_3$ (13.7 g, 6 equiv) and epichlorohydrin (1.42 ml, 1.1 equiv.) under an atmosphere of nitrogen. The mixture was refluxed for 2 days, cooled and filtered through a bed of Celite. The filtrate was concentrated to dryness, the residue was dissolved in $CH_2Cl_2$ and washed with brine. The organic layer was dried over anhydrous $Na_2SO_4$ and concentrated to give an oil which was chromatographed on silica gel eluting with 5:4 hexaneethyl acetate to give the title compound as an inseparable mixture of the two regioisomers. NMR ($CDCl_3$) (ppm): 2.1 (t, 1H), 3.5 (s, 2H), 3.7 (s, 3H), 3.85 (t, 2H), 4.15–4.4 (m, 3H) 6.85 (broad s, 3H).

EXAMPLE 34

Methyl (2- and 3-(4-acetyl-3-hydroxy-2-propylphenoxy)methyl-2,3-dihydro-1,4-benzodioxin-6-yl)acetates Following the procedure of Example 25, but starting with the mixture of compounds of Examples 33, there was obtained the mixture of title compounds as an oil.

Analysis, calculated for $C_{23}H_{26}O_7$: C, 66.65; H, 6.32. Found: C, 66.62; H, 6.48.

EXAMPLE 35

(2- and 3-(4-acetyl-3-hydroxy-2-propylphenoxy)methyl-2,3-dihydro-1,4-benzodioxin-6-yl)acetic acids Following the procedure of Example 26, but starting with the mixture of compounds of Example 34, there was obtained the mixture of title compounds as a beige solid, m.p. 95°–115°.

Analysis, calculated for $C_{22}H_{24}O_7$: C, 65.99; H, 6.04. Found: C, 65.95; H, 6.07.

EXAMPLE 36

Methyl 3-methylidene-2,4-dihydro-1,5-benzodioxin-7-yl acetate

To a solution of methyl 3,4-dihydroxyphenylacetate (1.2 g) in MEK (30 ml) was added $K_2CO_3$ (2.7 g) and 3-chloro-2-chloromethyl-1-propene. The mixture was refluxed for 18 hours, cooled to room temperature, filtered and the filtrate was evaporated to give an oil which was purified on a column of silica gel 120–230 mesh, (100 g) using as the eluant hexane/ethyl acetate (10:2). The title compound was obtained as a colorless oil.

NMR ($CDCl_3$) (ppm): 3.5 (s, 2H), 3.7 (s, 3H), 4.75 (s, 4H), 5.05 (s, 2H), 6.85 (s, 3H).

EXAMPLE 37

Methyl (3-oxidomethylidene-2,4-dihydro-1,5-benzodioxin-7-yl)acetate

Following the procedure of Example 23, but substituting the compound of Example 36 for the compound of Example 22, there was obtained the title compound as a colorless oil.

NMR ($CDCl_3$) (ppm): 2.85 (s, 2H), 3.5 (s, 2H), 3.7 (s, 3H), 4.25 (s, 4H), 6.9 (s, 3H).

EXAMPLE 38

Methyl (3-(4-acetyl-3-hydroxy-2-propylphenoxy)methyl-2,4-dihydro-3-hydroxy-1,5-benzodioxepin-7-yl)acetate To a solution of 2,4-dihydroxy-3-propylacetophenone (820 mg), and the compound of Example 37 (1.0 g) in MEK (30 ml) was added $K_2CO_3$ (1.73 g). The reaction mixture was refluxed under $N_2$ for 18 hours. The reaction mixture was cooled to room temperature, filtered, washed with acetone and the filtrate was evaporated to give an oil. $CH_2Cl_2$ was added and a solid formed. The mixture was filtered and the filtrate was washed with 0.1N NaOH (50 ml), brine and dried to give a yellow oil which was purified on a column of silica gel using hexane/ethyl acetate (2:1) as eluant. The title compound was recovered as an oil.

Analysis, calculated $C_{24}H_{28}O_8$: C, 64.85; H, 6.35. Found: C, 64.72; H, 6.37.

EXAMPLE 39

(3-(4-acetyl-3-hydroxy-2-propylphenoxy)methyl-2,4-dihydro-3-hydroxy-1,5-benzodioxepin-7-yl)acetic acid Following the procedure of Example 26, but substituting the compound of Example 38 for the compound of Example 25, there was obtained the title compound as a white foam.

Analysis, calculated for $C_{23}H_{26}O_8$: C, 64.17; H, 6.09. Found: C, 64.30; H, 5.93.

EXAMPLE 40

Methyl (3-hydroxymethyl-2,4-dihydro-1,5-benzodioxepin-7-yl)acetate

To a solution of the compound of Example 36 (2.34 g) in dry THF (20 ml) was added 1.04 m $BH_3$ in THF (3.9 ml) in portions (Note: $H_2$ gas was evolved and exothermic). The reaction mixture was stirred at room temperature under $N_2$ for 1.5 hours. $H_2O$ (0.66 ml) was then added ($H_2$ gas was evolved) and the mixture was stirred for 5 minutes. 3N NaOH (1.4 ml) was then added and, in portions, 30% H₂O₂ (1.4 ml) was added. The mixture was gently refluxed and stirred for 30 minutes. The reaction mixture was diluted with H₂O and extracted with ethyl acetate (3X). The combined organic layers were washed with brine, dried and evaporated to give the title compound as a crude oil. Chromatography on silica gel afforded the title compound which was used without further purification.

NMR (CDCl$_3$) (ppm): 2.3–2.6 (m, 1H), 2.8 (broad s, 1H), 3.5 (s, 2H), 32.7 (s, 3H), 3.8 (d, 2H), 4.25 (d, 4H), 6.9 (s, 3H).

EXAMPLE 41

Methyl (3-(4-acetyl-3-hydroxy-2-propylphenoxy)methyl-3,4-dihydro-2H-1,5-benzodioxepin-7-yl)acetate Following the procedure of Example 25, but substituting the compound of Example 40 for the compound of Example 24, there was obtained the title compound as an oil.

Analysis. calculated for C$_{24}$H$_{28}$O$_7$: C, 67.27; H, 6.59. Found: C, 67.38; H, 6.70.

EXAMPLE 42

(3-(4-acetyl-3-hydroxy-2-propylphenoxy)methyl-3,4-dihydro-2H-1,5-benzodioxepin-7-yl)acetic acid.

Following the procedure of Example 26, but substituting the compound of Example 41 for the compound of Example 25, there was obtained the title compound as a white foam.

Analysis, calculated for C$_{23}$H$_{26}$O$_7$: C, 66.65; H, 6.32. Found: C, 67.02; H, 6.50.

EXAMPLE 43

Methyl (4-hydroxy-3-allyloxyphenyl)acetate (less polar isomer)

A mixture of methyl 3,4-dihydroxyphenylacetate (1.82 g) and K$_2$CO$_3$ (4.1 g) in MEK (30 ml) at 25° was treated with allyl bromide (0.90 ml and the mixture was stirred in an atmosphere of N$_2$ for 2 hours at 60° (bath temperature). The reaction mixture was diluted with CH$_2$Cl$_2$ (100 ml), filtered and the filtrate was concentrated in vacuo. The residue was chromatographed in a column of silica gel (20–230 mesh) eluting with hexane-ethyl acetate-Et$_3$N (10:4:1) to give a mixture of regioisomers. This mixture was chromatographed over silica gel on a preparative HPLC (Waters 500) to give two fractions: (a) less polar (0.70 g) and (b) more polar (0.38 g).

NMR (CDCl$_3$) (ppm) (less polar isomer): 3.53 (s, 2H), 3.67 (s, 3H), 4.60 (m, 2H), 5.2–5.5 (m, 2H), 5.60 (1H, exchanges in D$_2$O), 6.03 (m, 1H), 6.80 (m, 3H). The less polar isomer corresponds to the title compound.

EXAMPLE 44

Methyl (4-(hydroxy-3-(2,3-oxidopropyl)oxyphenyl)acetate

A mixture of the compound of Example 43 (less polar isomer) (1.20 g) and m-CPBA (2.5 g) in CH$_2$Cl$_2$ (100 ml) and pH 7 buffer (350 ml) was stirred at room temperature for 24 hours. An additional amount of m-CPBA (2.0 g) was added and the mixture was stirred at room temperature for 60 hours. The organic layer was collected, washed with 10% sodium sulfide, 5% bicarbonate and brine. Evaporation of the dried (Na$_2$SO$_4$) organic solution gave the title compound as an oil. NMR (CDCl$_3$) (ppm): 2.73–3.00 (m, 2H), 3.10–3.47 (m, 2H), 3.50 (s, 2H), 3.67 (s, 3H), 4.15 (m, 2H), 6.83 (m, 3H).

EXAMPLE 45

Methyl (2-hydroxymethyl-2,3-dihydro-1,4-benzodioxin-6-yl)acetate

A mixture of the compound of Example 44 (0.66 g) and K$_2$CO$_3$ (0.60 g) in MEK (6 ml) was refluxed for 2 hours, cooled and filtered. The solid residue was washed with CH$_2$Cl$_2$ and the combined filtrate was concentrated. Preparative TLC eluting with ethyl acetate-hexane (1:1) gave the title compound as an oil.

NMR (CDCl$_3$) (ppm): 2.47 (1H, exchanges in D$_2$O), 3.50 (s, 2H), 3.67 (s, 3H), 3.80 (m, 2H), 4.03–4.37 (m, 3H), 6.80 (m, 3H).

EXAMPLE 46

Methyl (2-(4-acetyl-3-hydroxy-2-propylphenoxy)methyl-2,3-dihydro-1,4-benzodioxin-6-yl)acetate Following the procedure of Example 25, but substituting the compound of Example 45 for the compound of Example 24, there was obtained the title compound as a crystalline solid, m.p. 72°–75°.

EXAMPLE 47

(2-(4-Acetyl-3-hydroxy-2-propylphenoxy)methyl-2,3-dihydro-1,4-benzodioxin-6-yl)acetic acid Following the procedure of Example 26, but substituting the compound of Example 46 for the compound of Example 25, there was obtained the title compound as a solid, m.p. 143°–146°.

Analysis, calculated for C$_{22}$H$_{24}$O$_7$: C, 65.99; H, 6.04. Found: C, 66.08; H, 6.09.

Claims to the invention follow.

What is claimed is:

1. Compounds having the formula I:

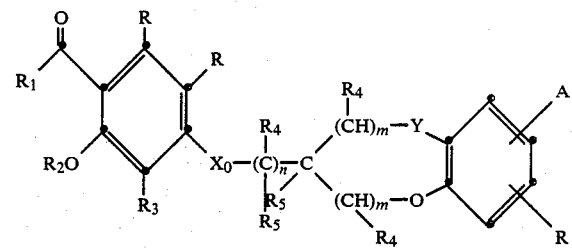

wherein
each R is independently H, OH, alkyl of 1 to 6 carbon atoms which may be straight chain or branched; alkenyl of 2 to 6 carbon atoms which may be straight chain or branched; trifluoromethyl; alkoxy of 1 to 6 carbon atoms which may be straight chain or branched; SH; thioalkyl of 1 to 6 carbon atoms which may be straight chain or branched; phenyl; phenyl substituted by alkyl of 1 to 3 carbon atoms or by halogen; benzyl; phenethyl; halogen; amino; N(R$_4$)$_2$ wherein each R$_4$ is independently H or alkyl of 1 or 6 carbon atoms which may be straight chain or branched; COOR$_4$; CH$_2$OR$_4$; formyl; CN; trifluoromethylthio; or nitro;

R$_1$ is alkyl of 1 to 6 carbon atoms which may be straight chain or branched; or alkoxy of 1 to 6 carbon atoms which may be straight chain or branched;

$R_2$ is H, alkyl of 1 to 6 carbon atoms which may be straight chain or branched; $R_4CO$; or $R_4OCH_2$;

$R_3$ is alkyl or 1 to 6 carbon atoms which may be straight chain or branched; or alkenyl of 3 to 6 carbon atoms which may be straight chain or branched;

Y is O or $CHR_4$;

A is

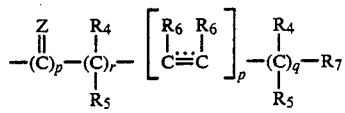

wherein

Z is O; S; $CH_2$; H/OH; alkenyl of 1-4 carbons; or N-$R_8$ wherein $R_8$ is OH, $N(R_4)_2$, alkyl or alkoxy of 1 to 6 carbon atoms, phenyl or phenyl substituted by alkyl or alkoxy groups of 1 to 3 carbon atoms, halogen, hydroxy, haloalkyl, COOH, CN, formyl or acyl of 1 to 6 carbon atoms;

each $R_5$ is independently H, OH, or alkyl of 1-4 carbons;

each $R_6$ is independently H, or alkyl of 1-4 carbons, and is absent when a triple bond is present;

$R_7$ is $COOR_4$; $CH_2OH$; CHO; tetrazole; $NHSO_2R_8$; hydroxymethylketone; CN; $CON(R_4)_2$; or

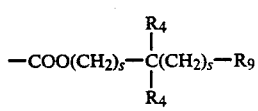

wherein each s is independently 0-3; $R_9$ is the radical W-$R_{10}$ wherein W is O, S or NH and $R_{10}$ is a hydrocarbon radical containing up to 21 carbon atoms;

r and q are each independently 0-20 provided that the total of r and q does not exceed 20; and each m is independently 0, 1, or 2;

each n is independently 0, 1, 2 or 3;

p is 0 or 1;

and a pharmaceutically acceptable salt or acid addition salt thereof.

2. The compounds of claim 1 having the formula:

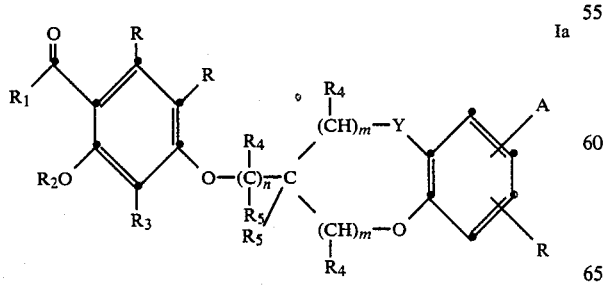

wherein:

A is

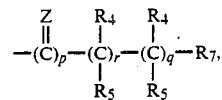

wherein

Z is O; S; H and OH; or N-$R_8$; and r and q are each independently 0-5.

3. The compounds of claim 1 wherein A is $CH_2CO_2H$ or $COCH_2CH_2CO_2H$.

4. The compounds of claim 3 having the formulae:

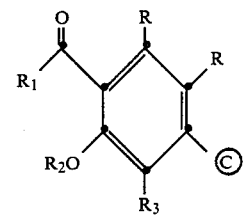

wherein Ⓒ is selected from:

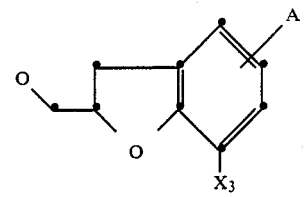

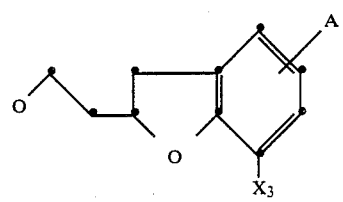

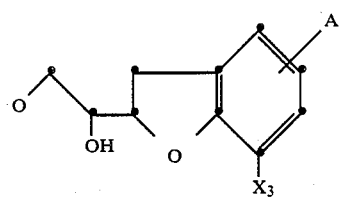

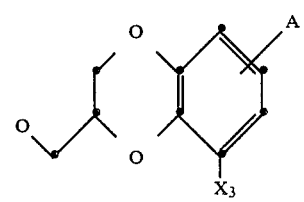

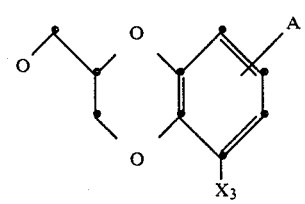

-continued

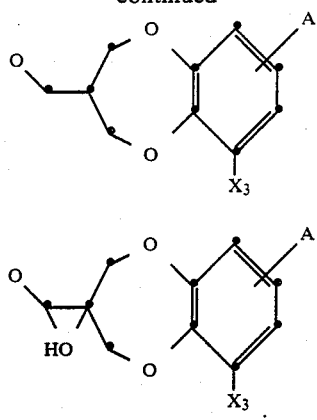

and wherein $X_3$ may be F or H.

5. The compounds of claim 1:
methyl 4-[2-(2-(4-acetyl-3-hydroxy-2-propylphenoxy)ethyl)-2,3-dihydrobenzo[b]furan-5-yl]-4-oxobutyrate;
4-[2-(2-(4-acetyl-3-hydroxy-2-propylphenoxy)ethyl)-2,3-dihydrobenzo[b]furan-5yl]-4-oxobutyric acid;
methyl [2-(1-hydroxy-2-(4-acetyl-3-hydroxy-2-propylphenoxy))ethyl-2,3-dihydrobenzo[b]furan-5-yl]acetate;
[2-(1-Hydroxy-2-(4-acetyl-3-hydroxy-2-propylphenoxy))ethyl-2,3-dihydrobenzo[b]furan-5-yl]acetic acid;
methyl 4- 2-(4-acetyl-3-hydroxy-2-propylphenoxymethyl)-2,3-dihydrobenzo[b]furan-5-yl)-4-oxobutyrate;
4-(2-(4-acetyl-3-hydroxy-2-propylphenoxymethyl)-2,3-dihydrobenzo[b]furan-5-yl)-4-oxobutyric acid;
methyl [2-(2-(4-acetyl-3-hydroxy-2-propylphenoxy)ethyl)-2,3-dihydrobenzo[b]furan-5-yl]acetate;
[2-(2-(4-acetyl-3-hydroxy-2-propylphenoxy)ethyl)-2,3-dihydrobenzo[b]furan-5-yl]acetic acid;
methyl (2-(4-acetyl-3-hydroxy-2-propylphenoxy)methyl-2,3-dihydrobenzo[b]furan-5-yl)acetate;
(2-(4-acetyl-3-hydroxy-2-propylphenoxy)methyl-2,3-dihydrobenzo[b]furan-5-yl)acetic acid;
methyl (2-(4-acetyl-3-hydroxy-2-propylphenoxy)methyl-7-fluoro-2,3-dihydrobenzo[b]furan-5-yl)acetate;
(3-(4-acetyl-3-hydroxy-2-propylphenoxy)methyl-7-fluoro-2,3-dihydrobenzo[b]furan-5-yl)acetic acid;
methyl (2-(4-acetyl-3-hydroxy-2-propylphenoxy)methyl-2,3-dihydro-1,4-benzodioxin-6-yl)acetate;
methyl (3-(4-acetyl-3-hydroxy-2-propylphenoxy)methyl-2,3-dihydro-1,4-benzodioxin-6-yl)acetate;
(2-(4-acetyl-3-hydroxy-2-propylphenoxy)methyl-2,3-dihydro-1,4-benzodioxin-6-yl)acetic acid;
(3-(4-acetyl-3-hydroxy-2-propylphenoxy)methyl-2,3-dihydro-1,4-benzodioxin-6-yl)acetic acid;
methyl (3-(4-acetyl-3-hydroxy-2-propylphenoxy)methyl-2,4-dihydro-3-hydroxy-1,5-benzodioxepin-7-yl)acetate;
(3-(4-acetyl-3-hydroxy-2-propylphenoxy)methyl-2,4-dihydro-3-hydroxy-1,5-benzodioxepin-7-yl)acetic acid;
methyl (3-(4-acetyl-3-hydroxy-2-propylphenoxy)methyl-3,4-dihydro-2H-1,5-benzodioxepin-7-yl)acetate;
(3-(4-acetyl-3-hydroxy-2-propylphenoxy)methyl-3,4-dihydro-2H-1,5-benzodioxepin-7-yl)acetic acid
methyl (2-(4-acetyl-3-hydroxy-2-propylphenoxy)methyl-2,3-dihydro-1,4-benzodioxin-6-yl)acetate;
(2-(4-acetyl-3-hydroxy-2-propylphenoxy)methyl-2,3-dihydro-1,4-benzodioxin-6-yl)acetic acid.

6. A composition containing a pharmaceutically effective amount of a compound of claim 1 and a pharmaceutical carrier.

7. A method of antagonizing leukotriene action in a mammal which comprises administering to said mammal a pharmaceutically effective amount of a compound of claim 1.

* * * * *